US012583804B2

(12) United States Patent
Zong et al.

(10) Patent No.: US 12,583,804 B2
(45) Date of Patent: Mar. 24, 2026

(54) PROCESS OF CONVERTING METHANOL TO OLEFINS

(71) Applicants:CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Hongyuan Zong, Shanghai (CN); Guozhen Qi, Shanghai (CN); Jing Cao, Shanghai (CN); Hongtao Wang, Shanghai (CN); Zhinan Yu, Shanghai (CN); Yijun Zheng, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 544 days.

(21) Appl. No.: 17/906,487

(22) PCT Filed: Mar. 12, 2021

(86) PCT No.: PCT/CN2021/080409
§ 371 (c)(1),
(2) Date: Sep. 16, 2022

(87) PCT Pub. No.: WO2021/185168
PCT Pub. Date: Sep. 23, 2021

(65) Prior Publication Data
US 2023/0137544 A1     May 4, 2023

(30) Foreign Application Priority Data
Mar. 19, 2020    (CN) .......................... 202010193702.1

(51) Int. Cl.
*C07C 1/20* (2006.01)
*B01J 8/18* (2006.01)
(Continued)

(52) U.S. Cl.
CPC .............. *C07C 1/20* (2013.01); *B01J 8/1809* (2013.01); *B01J 8/26* (2013.01); *B01J 29/85* (2013.01);
(Continued)

(58) Field of Classification Search
CPC ...... C07C 1/20; C07C 2529/85; B01J 8/1809; B01J 8/26; B01J 29/85; B01J 29/90;
(Continued)

(56) References Cited

U.S. PATENT DOCUMENTS

| | | |
|---|---|---|
| 4,499,327 A | 2/1985 | Kaiser |
| 6,166,282 A | 12/2000 | Miller |
| | (Continued) | |

FOREIGN PATENT DOCUMENTS

| | | |
|---|---|---|
| CN | 1723262 A | 1/2006 |
| CN | 101094829 A | 12/2007 |
| | (Continued) | |

OTHER PUBLICATIONS

Office Action issued on Jun. 14, 2024, by the Intellectual Property India in corresponding Indian Patent Application No. 202247058734 and an English translation of the Office Action (6 pages).
(Continued)

*Primary Examiner* — In Suk C Bullock
*Assistant Examiner* — Jason Y Chong
(74) *Attorney, Agent, or Firm* — Panitch Schwarze Belisario & Nadel LLP

(57) ABSTRACT

The present invention relates to a process of converting methanol to olefins, comprising: feeding a feedstock comprising methanol to a fluidized bed reactor to contact with catalysts to produce an olefin product, wherein the process at least partially deactivates the catalysts to format least (Continued)

partially deactivated catalysts; feeding spent catalysts from the at least partially deactivated catalysts to a regenerator for regeneration, thereby forming regenerated catalysts, and returning the activated catalysts from the regenerated catalysts to the reactor via a regenerated catalyst line; characterized in that on the regenerated catalyst line, the oxygen content by volume in the gas phase component at the outlet of the regenerated catalyst line is controlled to be less than 0.1%, preferably less than 0.05%, and more preferably less than 0.01%.

9 Claims, 1 Drawing Sheet

(51) Int. Cl.

| | | |
|---|---|---|
| *B01J 8/26* | (2006.01) | |
| *B01J 29/85* | (2006.01) | |
| *B01J 29/90* | (2006.01) | |
| *B01J 38/06* | (2006.01) | |

(52) U.S. Cl.
CPC .............. *B01J 29/90* (2013.01); *B01J 38/06* (2013.01); *C07C 2529/85* (2013.01)

(58) Field of Classification Search
CPC ... B01J 38/06; B01J 38/02; B01J 38/04; B01J 38/14; B01J 2208/00017; B01J 2208/00548; B01J 2208/00628; B01J 2208/00991; Y02P 20/584; Y02P 30/20; Y02P 30/40
See application file for complete search history.

(56) References Cited

U.S. PATENT DOCUMENTS

| | | |
|---|---|---|
| 2009/0240052 A1 | 9/2009 | Yokotani et al. |
| 2013/0178681 A1* | 7/2013 | Qi ............................ B01J 8/008 585/640 |

FOREIGN PATENT DOCUMENTS

| | | | |
|---|---|---|---|
| CN | 101279872 A | | 10/2008 |
| CN | 101293802 A | | 10/2008 |
| CN | 102276400 A | * | 12/2011 |
| CN | 101357874 B | | 9/2012 |
| CN | 107540493 A | | 1/2018 |
| CN | 107540495 A | | 1/2018 |
| CN | 113493365 A | | 10/2021 |

OTHER PUBLICATIONS

Examination Authority Report issued on Aug. 27, 2023, by the Iranian Patent Office in corresponding Iranian Patent Application No. 140150140003004740, with partial English translation of the Report (13 pages).

Office Action issued on Dec. 28, 2023, by the China National Intellectual Property Administration in corresponding Chinese Patent Application No. 202180022303.1 (9 pages).

International Search Report (PCT/ISA/210) with English translation, and Written Opinion (PCT/ISA/237) mailed on Jun. 11, 2021, by the China National Intellectual Property Administration as the International Searching Authority for International Application No. PCT/CN2021/080409.

Office Action issued on May 9, 2023, by Saudi Authority for Intellectual Property in corresponding Saudi Patent Application No. 522440572.

* cited by examiner

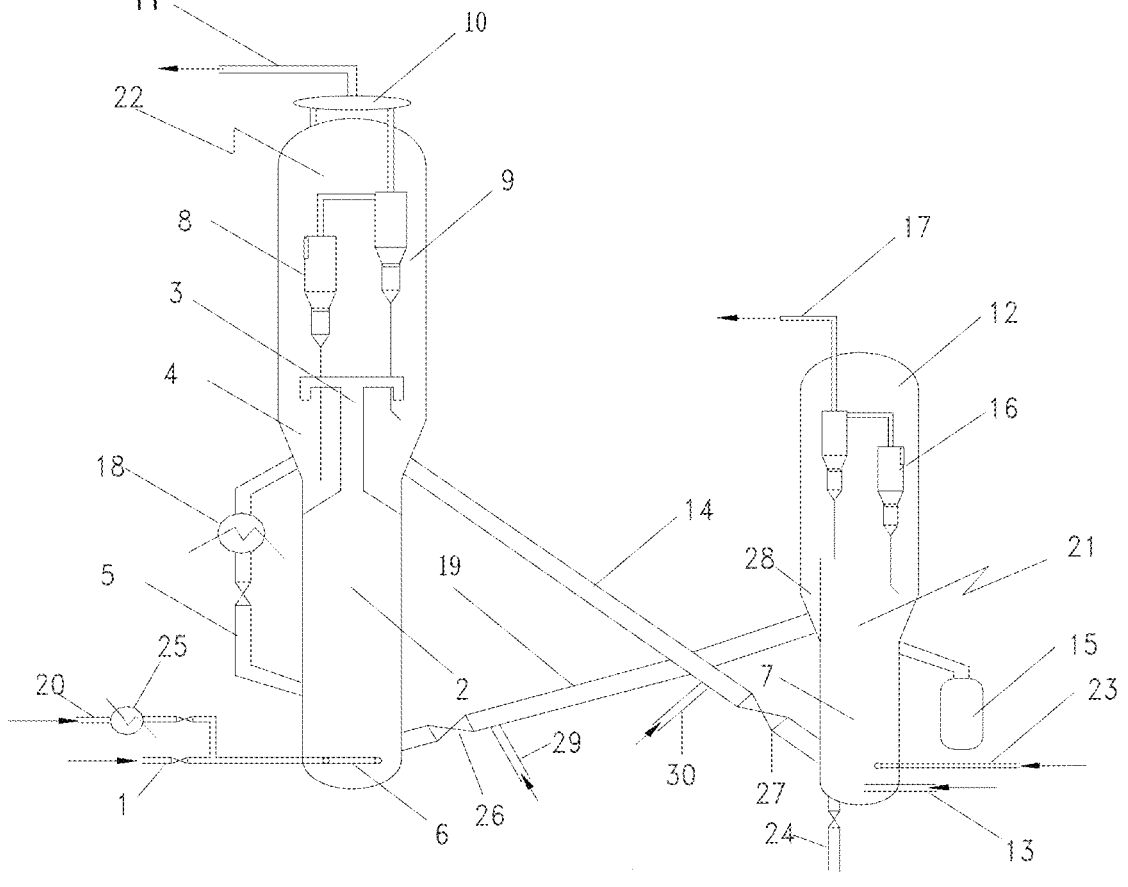

PROCESS OF CONVERTING METHANOL TO OLEFINS

TECHNICAL FIELD

The present invention relates to a process for the conversion of methanol to olefins.

BACKGROUND

Lower olefins comprise mainly ethylene and propylene, which are two important basic chemical raw materials, and the demand of the lower olefins is increasing continuously. Ethylene is used to produce various polyethylene plastics, vinyl chloride, ethylene oxide, ethylbenzene, and ethanol. Propylene is used to produce various polypropylene plastics, acrylonitrile and propylene oxide. In addition to cracking petroleum products to provide lower olefins, one of the preferred conversion processes is a process from oxygenate to olefins. When methanol is used as the primary oxygenate, the process is referred to as an MTO process.

In an MTO reactor, under certain conversion conditions, methanol or a mixture of methanol and a diluent is contacted with a MTO catalyst to be converted into lower olefins. One of the preferred MTO catalysts are a silicoaluminophosphate (SAPO) molecular sieve catalyst, particularly SAPO-34, because of its high selectivity to ethylene and propylene. Document U.S. Pat. No. 4,499,327 makes detailed studies on the application of a silicoaluminophosphate molecular sieve catalyst in a process for preparing olefins by methanol conversion, and proposes SAPO-34 as a preferred catalyst for an MTO process. The SAPO-34 catalyst has high selectivity and activity for lower olefin, and can ensure that the reaction duration for converting methanol to the lower olefin is less than 10 seconds, even up to reach the reaction duration range of a riser.

Document U.S. Pat. No. 6,166,282 discloses a technology and reactor for converting methanol to lower olefins, which uses a fast fluidized bed reactor, wherein after the gas phase is reacted in a dense phase reaction zone having a lower gas velocity, the gas phase rises to a fast separation zone having a dramatically reduced inner diameter, and a special gas-solid separation device is used for primarily separating most of the entrained catalysts. As the product gas and the catalyst are rapidly separated after the reaction, the occurrence of secondary reaction is effectively prevented. Through simulation calculation, it can be seen that compared with the traditional bubbling fluidized bed reactor, the internal diameter of the fast fluidized bed reactor and the required inventory of the catalyst are greatly reduced. The carbon-based yield of the lower olefin in the process is generally about 77%.

Document CN101357874B discloses a method for producing lower olefins from methanol or dimethyl ether, which comprises the following steps: a, providing a fast fluidized bed reactor; b. feeding a raw material containing methanol or dimethyl ether into a fast bed reaction zone of the reactor to contact with catalysts, and converting the raw material into a product stream containing ethylene and propylene under effective conditions; c. after the product stream is separated, feeding most of the catalysts into a second dense phase stripping zone; d, contacting the catalysts entering the second dense phase stripping zone with a stripping medium to remove the entrained product stream; and e. dividing the stripped, hot catalysts into at least two portions, where at least the first portion is returned to the bottom of the fast bed reaction zone and at least the second portion is fed to a regenerator.

Document CN1723262A discloses a multi-stage riser reactor equipped with a central catalyst loop for the process of converting oxides into lower olefins, which comprises a plurality of riser reactors, a gas-solid separation zone, a plurality of shift elements, and the like, wherein each riser reactor has a port for injecting catalysts, and the separation zone separates the catalyst from the product gas. The yield of the lower olefins, calculated as carbon, in the process is generally 75-80%.

However, with the increasing demand of ethylene and propylene in the market, higher requirements are raised on the production technology of the lower olefins.

SUMMARY OF THE INVENTION

The inventors of the invention discover that in the reaction-regeneration process during converting methanol into lower olefins, because of different environments in the reaction process and the regeneration process, presence of the circulation of the catalyst, and porous nature of the catalyst solid, it is inevitable to carry one medium to another, thereby influencing the reaction process or the regeneration process. For example, excessive amount of oxygen brought into the reactor can cause the increase of byproducts of alkyne, dialkene, oxygenate and the like, and the excessive generation of these impurities can seriously influence the separation process. Excessive amount of steam brought into a high-temperature regenerator (the regeneration temperature generally exceeds 650° C.) can result in the volume of steam in the catalyst pore channel being sharply enlarged due to the excessive temperature difference, so that the catalyst is broken, the content of fine powder is increased, and the loss of the catalyst is increased. The inventors of the invention discover through a great deal of research that the problems can be solved by arranging a catalyst flow rate control device on the spent catalyst line and the regenerated catalyst line which connect the reactor and the regenerator, and reasonably arranging a stripping or degassing device, a purging or loosening medium upstream the inlet of the catalyst flow rate control device, strengthening the stripping and degassing effects, and strictly controlling the amount of oxygen entering the reactor and the amount of steam entering the regenerator. The present invention has been completed based on these discoveries.

In general, for example, the invention provides a process of converting methanol to olefins, the process comprising: regenerating the at least partially deactivated catalysts produced in the conversion process into a regenerator, and returning the regenerated catalysts formed thereby to said reactor via a regenerated catalyst line; wherein, a second catalyst flow rate control device is arranged on the regenerated catalyst line, and the second catalyst flow rate control device controls the oxygen volume content in the gas phase component at the outlet of the regenerated catalyst line to be less than 0.1%.

Preferably, in the process above, the at least partially deactivated catalysts are fed into the regenerator for regeneration through a spent catalyst line, and the spent catalyst line is equipped with a first catalyst flow rate control device, which controls the volume content of steam in the gas phase component at the outlet of the first catalyst flow rate control device to be less than 0.1%.

Still preferably, in the process above, a stripping branch line of the stripping medium is arranged on the line between the inlet of the spent catalyst line and the first catalyst flow rate control device; and a degassing branch line of the degassing medium is arranged on a line between the inlet of the regenerated catalyst line and the second catalyst flow rate control device.

For the purposes of the present invention, "at least partially deactivated catalyst" encompasses the catalysts which have been entirely deactivated and is therefore used interchangeably with the term "deactivated catalyst" in the present invention.

Specifically, the present invention provides embodiments such as the following:

1. A process of converting methanol to olefins, comprising: feeding a feedstock comprising methanol to a fluidized bed reactor to contact with catalysts to produce an olefin product, wherein the process at least partially deactivates the catalysts to form at least partially deactivated catalysts; feeding spent catalysts from the at least partially deactivated catalysts to a regenerator for regeneration, thereby forming regenerated catalysts, and returning the activated catalysts from the regenerated catalysts to the reactor via a regenerated catalyst line; characterized in that on the regenerated catalyst line, the oxygen content by volume in the gas phase component at the outlet of the regenerated catalyst line is controlled to be less than 0.1%, preferably less than 0.05%, and more preferably less than 0.01%.

2. The process of embodiment 1, wherein the spent catalysts are regenerated by feeding the spent catalysts through a spent catalyst line to a regenerator, where on the spent catalyst line, the steam content by volume in the gas phase component at the outlet of the spent catalyst line is controlled to be less than 0.1%, preferably less than 0.05%, and more preferably less than 0.01%.

3. The process according to embodiment 2, characterized in that additional stripping is performed on the line between the inlet of the spent catalyst line and the first catalyst flow rate control device; and/or additional degassing is performed on the line between the regenerated catalyst line inlet to the second catalyst flow rate control device.

4. The process according to embodiment 3, characterized in that regulations of the medium flow rates are respectively carried out on each of the stripping branch line of the stripping medium and the degassing branch line of the degassing medium, preferably by means of a regulating valve or orifice plate.

5. The process according to any one of the preceding embodiments, characterized in that the at least partially deactivated catalysts are subjected to steam stripping by at least one stage of steam stripping medium in a steam stripper to provide the spent catalysts; the spent catalysts is fed into the regenerator through the spent catalyst line for regeneration to provide the regenerated catalysts; the regenerated catalysts are degassed in a degassing tank by using at least one stage of degassing medium, to provide the activated catalyst; and the activated catalysts are returned to the reactor through the regenerated catalyst line; wherein the stripping medium is steam and the degassing medium is steam or nitrogen.

6. The process of embodiment 5, characterized in that the spent catalyst line is operated under conditions of: a temperature of 200-500° C., preferably 250-450° C.; a density of the catalyst of 50-500 kg/m$^3$, preferably 150-400 kg/m$^3$; and a volume ratio of the steam to the spent catalysts of 0.001-0.5, preferably 0.01-0.1; and the regenerated catalyst line is operated under conditions of: a temperature of 300-700° C., preferably 400-650° C.; a density of the catalyst of 50-500 kg/m$^3$, preferably 150-400 kg/m$^3$; a volume ratio of the degassing medium to the regenerated catalysts of 0.001 to 0.5, preferably 0.01 to 0.1.

7. The process of embodiment 1, characterized in that the catalyst active component is a silicoaluminophosphate molecular sieve comprising SAPO-34.

8. A device for carrying out the process of converting methanol to olefins of any one of the preceding embodiments, comprising:
a fluidized bed reactor, for receiving a methanol feedstock and contacting it with catalysts to produce an olefin product, wherein the process at least partially deactivates the catalysts to produce at least partially deactivated catalysts;
a regenerator, for regenerating the spent catalysts from the fluidized bed reactor to provide regenerated catalysts;
a regenerated catalyst line, for returning the activated catalysts to the reactor therethrough; and
a second catalyst flow rate control device disposed on the regenerated catalyst line, which is configured to control the oxygen content by volume in the gas phase component at the outlet of the regenerated catalyst line to be less than 0.1%, preferably less than 0.05%, more preferably less than 0.01%.

9. The device according to embodiment 8, further comprising a spent catalyst line for feeding the deactivated catalysts into the regenerator for regeneration, wherein the spent catalyst line is provided with a first catalyst flow rate control device, which is configured to control the steam content by volume of the gas phase component at the outlet of the spent catalyst line to be less than 0.1%, preferably less than 0.05%, more preferably less than 0.01%.

10. The device according to embodiment 9, characterized in that a stripping branch line of the stripping medium is arranged on a line between the inlet of the spent catalyst line and the first catalyst flow rate control device, for performing additional stripping; and a degassing branch line of the degassing medium is arranged on a line between the inlet of the regenerated catalyst line and the second catalyst flow rate control device, for carrying out additional degassing.

11. The device of embodiment 9, further comprising:
a stripper, for carrying out at least one stage of stripping by a medium stripping on the at least partially deactivated catalyst, to provide the spent catalysts;
a degassing tank, for degassing the regenerated catalysts in the degassing tank by at least one stage of degassing medium, to provide the activated catalyst;
characterized in that the inlet of the stripper is connected with the separation zone of the reactor, and the outlet of the stripper is connected with the inlet of the spent catalyst line; the inlet of the degassing tank is connected with the dilute phase section of the regenerator, and the outlet of the degassing tank is connected with the inlet of the regenerated catalyst line.

In an exemplary embodiment of the invention, the stripper is arranged inside the reactor. In another exemplary embodiment of the invention, the stripper is arranged outside the reactor.

In an exemplary embodiment of the invention, the degassing tank is arranged inside the regenerator. In another exemplary embodiment of the invention, the degassing tank is arranged outside the regenerator.

In a preferred embodiment of the invention, at least one layer of baffle is equipped in the stripper and at least one layer of baffle is equipped in the degassing tank, where the degassing medium is fed into the degassing tank in sections.

12. The device according to embodiment 11, characterized in that the top of the stripper is equipped with a gas phase outlet connected to the separation zone of the reactor, and the top of the degassing tank is equipped with a gas phase outlet connected to the dilute phase section of the regenerator or a flue gas line of the regenerator outlet.

13. The device of embodiment 9, characterized in that the first catalyst flow rate control device and the second catalyst flow rate control device are each independently a pneumatic or hydraulic one-way slide valve.

14. The device of embodiment 8, characterized in that the fluidized bed reactor is in a dense phase form, turbulent form or fast fluidized form.

Technical Effects

According to the process of the invention, the product has less impurities.

According to the process of the invention, the catalyst loss is small.

DESCRIPTION OF DRAWINGS

FIG. 1 is a schematic flow chart of the process according to the present invention.

In FIG. 1, 1 denotes a feedstock of the reactor;

2 denotes a reaction zone of the reactor;

3 denotes a gas-solid rapid separation zone;

4 denotes a stripper;

5 denotes an external circulation inclined tube of the reactor;

6 denotes a feedstock distributor;

7 denotes a regeneration zone of the regenerator;

8 denotes a gas-solid cyclone separator of the reactor;

9 denotes a separation zone of the reactor;

10 denotes a gas collecting chamber;

11 denotes a product gas outlet line;

12 denotes a dilute phase section of the regenerator;

13 denotes a regeneration medium inlet line;

14 denotes a spent catalyst line (or a spent inclined line);

15 denotes an external heat remover of the regenerator;

16 denotes a gas-solid cyclone separator of the regenerator;

17 denotes a regenerated flue gas outlet line;

18 denotes an external heat remover of the reactor;

19 denotes a regenerated catalyst line (or a regenerated inclined pipe);

20 denotes a line for introducing steam into the reactor;

21 denotes a regenerator;

22 denotes a reactor;

23 denotes a burning oil inlet line;

24 denotes a bottom catalyst charging/discharging line of the regenerator;

25 denotes an auxiliary heating furnace;

26 denotes a second catalyst flow rate control device (regeneration inclined line slide valve);

27 denotes a first catalyst flow rate control device (spent inclined line slide valve);

28 denotes a degassing tank;

29 denotes a degassing branch line of the degassing medium; and 30 denotes a stripping branch line of the stripping medium.

EMBODIMENTS OF THE INVENTION

The present invention will be further illustrated in more detail below, while it should be understood that the scope of the invention is not restricted by the embodiments, but is defined by the appended claims.

All publications, patent applications, patents, and other references mentioned in this specification are herein incorporated by reference in their entirety. Unless defined specifically, all technical and scientific terms used herein have the same meaning as commonly understood by those skilled in the art to which this invention belongs. In case of conflict, the present specification, including definitions, will control.

When the present specification mentions a material, substance, method, step, device, or component, etc. with the derivative words "known to those skilled in the art", "prior art" or the like, the term derived is intended to cover those conventionally used in the field of the present application, but also cover those that are not currently known, whilst will become known in the art to be useful for the similar purposes.

In the context of this specification, the methods for preparing SAPO molecular sieves or SAPO molecular sieve catalysts are well known in the art.

In the context of the present specification, the term "at least partially deactivated catalyst" or "deactivated catalyst" is used to refer to catalysts whose activity is at least partially reduced after passing through a reaction zone.

In the context of this specification, the term "spent catalyst" is used to refer to the catalyst that is delivered from the reactor (e.g., via a spent catalyst line) to the regenerator for regeneration.

In the context of the present specification, the term "regenerated catalyst" is used to refer to the catalyst obtained after regeneration (e.g., by coke burning) in the regeneration zone of the regenerator.

In the context of this specification, the term "activated catalyst" is used to refer to catalyst that is sent (e.g., via a regenerated catalyst line) to the reactor for reaction after regeneration and optional further treatment (i.e., completion of regeneration) in the regenerator.

All percentages, parts, ratios, etc. involved in this specification are indicated by weight and pressures are gauge pressures unless explicitly indicated otherwise.

may be combined to form an embodiment, and the resulting embodiment is a part of the original disclosure of this specification, and is within the protection scope of the invention.

An exemplary embodiment A of the present invention is shown in FIG. 1. Referring to FIG. 1, a stream comprising a methanol feedstock is fed via a feed line 1, and optionally through a feedstock distributor 6, into the reaction zone 2 of the reactor 22 and contacted with molecular sieve catalysts to react to produce a product comprising lower olefins, wherein the catalysts are at least partially deactivated. The at least partially deactivated catalysts are fed into the separation area 9 of the reactor through the gas-solid rapid separation area 3, wherein most of the at least partially deactivated catalysts separated by the gas-solid rapid separation device 3 are fed into a stripper 4, and the gas phase product separated by the gas-solid rapid separation device 3 and a part of the at least partially deactivated catalysts not separated by the gas-solid rapid separation device are fed into the cyclone separator 8 for further separation. The at least partially deactivated catalysts separated by the cyclone 8 are also returned to the stripper 4 via the dipleg of the cyclone 8. The gas-phase product separated by the gas-solid rapid separation device 3 and the gas-phase product separated by the cyclone separator 8 are fed to the subsequent separation working section through a gas collection chamber 10 and an outlet line 11.

The at least partially deactivated catalysts separated by the gas-solid rapid separation zone 3 and by the cyclone separator 8 are stripped to provide the spent catalysts, which are divided into two parts, where one part is returned to the bottom of the reaction zone 2 through the catalyst outer circulation inclined line 5; and another part is fed into the regenerator 21 through spent catalyst line 14. The spent catalyst line 14 is equipped with a first catalyst flow rate control device 27 configured to control the steam content by volume of the gas phase component at the outlet of the spent catalyst line to be less than 0.1%, preferably less than 0.05%, more preferably less than 0.01%.

The spent catalysts are regenerated in the regeneration zone 7 of the regenerator 21, where the regeneration medium used may be those conventionally used in the art, such as air, oxygen, etc. The regeneration is preferably carried out by coke burning, to provide the regenerated catalysts. Flue gas generated by coke burning is passed through a cyclone separator 16 and then fed into a subsequent energy recovery system through a flue gas outlet line 17. The regenerated catalysts are fed into the degassing tank 28 connected to the dilute phase section 12 at the upper part of the regenerator 21 and are degassed in the degassing tank 28 by at least one stage of degassing medium to provide the activated catalyst. The activated catalysts are returned to the reaction zone 2 of the reactor via the regenerated catalyst line 19. The regenerated catalyst line 19 is equipped with a second catalyst flow rate control device 26 configured to control the oxygen content by volume of the gas phase component at the outlet of the regenerated catalyst line to be less than 0.1%, preferably less than 0.05%, more preferably less than 0.01%.

In the above embodiment A, preferably, the line 20 for introducing steam into the reactor is equipped with an auxiliary heating furnace 25, which line 20 is combined with the feed line 1 and then is fed into the reactor 22. According to the invention, for example, one of the functions of the steam fed through the steam line 20 is to serve for starting-up heating; accordingly, the auxiliary furnace 25 assists in reaching the reaction start-up temperature during the charging.

In the above embodiment A, preferably, the catalyst external circulation inclined line 5 of the reactor 22 is equipped with an external reactor heat remover 5 for removing heat generated by the reaction in the reactor, so as to achieve the purpose of controlling the reaction temperature required by the reaction zone.

In the above embodiment A, preferably, the bottom of the regenerator 21 is equipped with a catalyst charging/discharging line 24, for introducing the catalyst into the regenerator during start-up or normal operation or for discharging the catalyst from the regenerator during shutdown.

In the above embodiment A, preferably, the regeneration medium is added to the regenerator 21 through the regeneration medium inlet line 13; and a burning oil is added to the regenerator 21 through the burning oil inlet line 23.

In the above embodiment A, preferably, the regenerator 21 is equipped with an external regenerator heat remover 15 for removing heat generated by the reaction in the regenerator 21, so as to achieve the purpose of controlling the regeneration temperature required by the regenerator.

In one embodiment of the present invention, optionally, a group of steam stripping branch lines are equipped at intervals on the line between the inlet of the spent catalyst line and the catalyst flow rate control device, and each group of the steam stripping branch lines is arranged radially around the line.

In one embodiment of the invention, optionally, a group of degassing branch line of the degassing medium is equipped at intervals on the line between the inlet of the regenerated catalyst line and the catalyst flow rate control device, and each group of the degassing branch lines of the degassing medium is arranged radially around the line.

In one embodiment of the invention, optionally, both the steam stripping branch line and the degassing branch line of the degassing medium are equipped with orifice plates. The dimensions of the orifice plates are selected according to the design. The medium flow of each branch is fixed without manual adjustment. Each branch line is equipped with a switch valve.

In one embodiment of the invention, the stripping branch line of the stripping medium and the degassing branch line of the degassing medium optionally have not only a loosening function but also an additional stripping or degassing function.

The present invention will be described below by way of Examples, which do not represent limitations on the scope of the present invention.

Example 1

Referring to FIG. 1, the exemplary embodiment A of the present invention was used.

The active component of the catalyst was a silicoaluminophosphate molecular sieve comprising SAPO-34, and the fluidized bed reactor was in a fast fluidization form. The catalyst flow rate control device was a pneumatic one-way slide valve. The at least partially deactivated catalysts in the reactor were stripped with a one-stage stripping medium. The spent catalysts were fed into the regenerator for regeneration through the spent catalyst line. The regenerated catalysts were degassed via a degassing medium. The regenerated activated catalysts were returned to the reactor through the regenerated catalyst line. The stripping medium was steam, and the degassing medium was steam. The steam stripping process was carried out in a steam stripper, wherein the inlet of the steam stripper was connected with the reactor, and the outlet of the steam stripper was connected with the inlet of the spent catalyst line. The degassing process was carried out in a degassing tank, which was disposed inside the regenerator. The inlet of the degassing tank was connected with the regenerator, and the outlet of the degassing tank was connected with the inlet of the regenerated catalyst line. A steam stripping branch line was arranged on the line between the inlet of the spent catalyst line and the catalyst flow rate control device, and the steam stripping branch line was radially arranged around the line. A degassing branch line of the degassing medium was arranged on the line between the inlet of the regenerated catalyst line and the catalyst flow rate control device, and the degassing branch line of the degassing medium was radially arranged around the line. Both the steam stripping branch line and the degassing branch line of the degassing medium were equipped with orifice plates, and each branch line was equipped with a switch valve. The stripper was equipped with 5 layers of baffles which were arranged in a staggered way. The degassing tank was equipped with 2 layers of baffles, and the degassing medium was fed into the degassing tank in two sections. The top of the stripper was equipped with a gas phase outlet connected with the reactor main body, and the top of the degassing tank was equipped with a gas phase outlet connected with the dilute phase section of the regenerator.

The spent catalyst line was operated under conditions of: a temperature of 200° C., a density of the catalyst of 50 kg/m$^3$, and a volume ratio of the steam to the spent catalysts of 0.5. The regenerated catalyst line was operated under conditions of: a temperature of 300° C., a catalyst density of 50 kg/m and a volume ratio of the degassing medium to the regenerated catalysts of 0.5. The steam content by volume in the gas phase component at the outlet of the catalyst flow rate control device on the spent catalyst line was 0.05%, and the oxygen content by volume in the gas phase component at the outlet of the catalyst flow rate control device on the regenerated catalyst line was 0.005%.

By analysis, the product gas at the outlet of the reactor comprised, in weight fractions, less than 100 ppm of oxygenates (the sum of aldehyde, ketone and acid) and less than 1 ppm of acetylene, and the catalyst loss was reduced by 4% within 3 months.

Example 2

The conditions and procedures described in Example 1 were essentially followed, except those specifically indicated below. The fluidized bed reactor is in a dense phase fluidized form. The catalyst flow rate control device was a hydraulic one-way slide valve. The at least partially deactivated catalysts in the reactor were stripped with two-stage stripping mediums. The degassing medium was nitrogen gas. The stripper was equipped with 2 layers of baffles which were arranged in a staggered way. The degassing tank was equipped with 4 layers of baffles, and the degassing medium was fed into the degassing tank in two sections. The top of the degassing tank was equipped with a gas phase outlet connected with the flue gas line of the regenerator outlet.

The spent catalyst line was operated under conditions of: a temperature of 490° C., a density of the catalyst of 480 kg/m$^3$, and a volume ratio of the steam to the spent catalysts of 0.002. The regenerated catalyst line was operated under conditions of: a temperature of 680° C., a catalyst density of 460 kg/m and a volume ratio of the degassing medium to the regenerated catalysts of 0.003. The steam content by volume in the gas phase component at the outlet of the catalyst flow rate control device on the spent catalyst line was 0.03%, and the oxygen content by volume in the gas phase component at the outlet of the catalyst flow rate control device on the regenerated catalyst line was 0.008%.

By analysis, the product gas at the outlet of the reactor comprised, in weight fractions, less than 50 ppm of oxygenates and less than 1 ppm of acetylene, and the catalyst loss was reduced by 6% within 3 months.

Example 3

The conditions and procedures described in Example 1 were followed. The spent catalyst line was operated under conditions of: a temperature of 400° C., a density of the catalyst of 380 kg/m$^3$, and a volume ratio of the steam to the spent catalysts of 0.01. The regenerated catalyst line was operated under conditions of: a temperature of 630° C., a catalyst density of 380 kg/m and a volume ratio of the degassing medium to the regenerated catalysts of 0.01. The steam content by volume in the gas phase component at the outlet of the catalyst flow rate control device on the spent catalyst line was 0.01%, and the oxygen content by volume in the gas phase component at the outlet of the catalyst flow rate control device on the regenerated catalyst line was 0.01%.

By analysis, the product gas at the outlet of the reactor comprised, in weight fractions, less than 150 ppm of oxygenates and less than 1 ppm of acetylene, and the catalyst loss was reduced by 10% within 3 months.

Example 4

The conditions and procedures described in Example 1 were followed. The spent catalyst line was operated under conditions of: a temperature of 480° C., a density of the catalyst of 450 kg/m$^3$, and a volume ratio of the steam to the spent catalysts of 0.005. The regenerated catalyst line was operated under conditions of: a temperature of 670° C., a catalyst density of 380 kg/m and a volume ratio of the degassing medium to the regenerated catalysts of 0.005. The steam content by volume in the gas phase component at the outlet of the catalyst flow rate control device on the spent catalyst line was 0.001%, and the oxygen content by volume in the gas phase component at the outlet of the catalyst flow rate control device on the regenerated catalyst line was 0.0004%.

By analysis, the product gas at the outlet of the reactor comprised, in weight fractions, less than 40 ppm of oxygenates and less than 1 ppm of acetylene, and the catalyst loss was reduced by 15% within 3 months.

Comparative Example 1

The procedures described in Example 1 were followed. The steam content by volume in the gas phase component at the outlet of the catalyst flow rate control device on the spent catalyst line was 0.21%, and the oxygen content by volume in the gas phase component at the outlet of the catalyst flow rate control device on the regenerated catalyst line was 0.18%.

The product gas at the outlet of the reactor comprised, in weight fractions, as high as 308 ppm of oxygenates and as high as 3 ppm of acetylene.

Obviously, the process according to the present invention could achieve the purpose of improving the yield of the lower olefins and thus was able to be used for the industrial production of the lower olefins.

The invention claimed is:

1. A process of converting methanol to olefins, comprising: feeding a feedstock comprising methanol to a fluidized bed reactor to contact with catalysts to produce an olefin product, wherein the process at least partially deactivates the catalysts to form at least partially deactivated catalysts; feeding spent catalysts from the at least partially deactivated catalysts to a regenerator for regeneration, thereby forming regenerated catalysts, and returning activated catalysts from the regenerated catalysts to the reactor via a regenerated catalyst line; wherein on the regenerated catalyst line, an oxygen content by volume in a gas phase component at an outlet of the regenerated catalyst line is controlled to be 0.01% or less than 0.01%, and the spent catalysts are regenerated by feeding the spent catalysts through a spent catalyst line to a regenerator, wherein on the spent catalyst line, a steam content by volume in the gas phase component at an outlet of the spent catalyst line is controlled to be 0.05% or less than 0.05%.

2. The process according to claim 1, wherein additional stripping is performed on a line between an inlet of the spent catalyst line and a first catalyst flow rate control device; and/or additional degassing is performed on a line between an inlet of the regenerated catalyst line and a second catalyst flow rate control device.

3. The process according to claim 2, wherein regulations of medium flow rates are respectively carried out on each of the stripping branch line of the stripping medium and the degassing branch line of the degassing medium.

4. The process according to claim 2, wherein regulations of the medium flow rates are respectively carried out on each of the stripping branch line of the stripping medium and the degassing branch line of the degassing medium by means of a regulating valve or orifice plate.

5. The process according to claim 1, wherein the at least partially deactivated catalysts are subjected to steam stripping by at least one stage of steam stripping medium in a steam stripper, to provide the spent catalysts;

the spent catalysts are fed into the regenerator through a spent catalyst line for regeneration to provide the regenerated catalysts;

the regenerated catalysts are degassed in a degassing tank by using at least one stage of degassing medium, to provide the activated catalyst; and the activated catalysts are returned to the reactor through the regenerated catalyst line;

wherein the stripping medium is steam and the degassing medium is steam or nitrogen.

6. The process according to claim 5, wherein the spent catalyst line is operated under conditions of: a temperature of 200-500° C.; a density of the catalyst of 50-500 kg/m$^3$; and a volume ratio of the steam to the spent catalysts of 0.001-0.5; and the regenerated catalyst line is operated under conditions of: a temperature of 300-700° C.; a density of the catalyst of 50-500 kg/m$^3$; a volume ratio of the degassing medium to the regenerated catalysts of 0.001 to 0.5.

7. The process according to claim 5, wherein the spent catalyst line is operated under conditions of: a temperature of 250-450° C.; a density of the catalyst of 150-400 kg/m$^3$; and a volume ratio of the steam to the spent catalysts of 0.01-0.1; and the regenerated catalyst line is operated under conditions of: a temperature of 400-650° C.; a density of the catalyst of 150-400 kg/m$^3$; a volume ratio of the degassing medium to the regenerated catalysts of 0.01 to 0.1.

8. The process according to claim 1, wherein each of the catalysts contains a catalyst active component and wherein the catalyst active component is a silicoaluminophosphate molecular sieve comprising SAPO-34.

9. The process according to claim 1, wherein on the spent catalyst line, the steam content by volume in the gas phase component at the outlet of the spent catalyst line is controlled to be less than 0.01%.

* * * * *